United States Patent [19]
Henry

[11] Patent Number: 5,990,174
[45] Date of Patent: Nov. 23, 1999

[54] AQUEOUS COMPOSITION

[75] Inventor: William John Henry, Dollar, United Kingdom

[73] Assignee: Zeneca Limited, London, United Kingdom

[21] Appl. No.: 08/063,330

[22] Filed: May 19, 1993

Related U.S. Application Data

[63] Continuation of application No. 07/784,226, Oct. 28, 1991, abandoned.

[30] Foreign Application Priority Data

Nov. 6, 1990 [GB] United Kingdom .................. 9024133

[51] Int. Cl.$^6$ ..................................................... A01N 37/52
[52] U.S. Cl. ........................... 514/635; 514/634; 514/636
[58] Field of Search .................................. 514/634, 635, 514/636

[56] References Cited

U.S. PATENT DOCUMENTS

| | | | |
|---|---|---|---|
| 3,639,631 | 2/1972 | Badcock et al. | 514/635 |
| 4,661,523 | 4/1987 | Disch | 514/635 |
| 5,030,659 | 7/1991 | Bansemir et al. | 514/635 |

FOREIGN PATENT DOCUMENTS

| | | |
|---|---|---|
| 110568 | 6/1984 | European Pat. Off. . |
| 0324211 | 1/1988 | European Pat. Off. . |
| 324211 | 7/1989 | European Pat. Off. . |
| 379256 | 7/1990 | European Pat. Off. . |
| 91119 | 10/1948 | New Zealand . |
| 95714 | 9/1950 | New Zealand . |
| 118495 | 5/1958 | New Zealand . |
| 702268 | 1/1954 | United Kingdom . |
| 1152243 | 5/1969 | United Kingdom . |
| 2187097 | 9/1987 | United Kingdom . |

OTHER PUBLICATIONS

Derwent Publications Ltd., London WPI, Acct. No. 75–12733W/08 (1974).

*Primary Examiner*—Allen J. Robinson
*Attorney, Agent, or Firm*—Pillsbury Madison & Sutro LLP

[57] ABSTRACT

A aqueous medium containing a biguanide, particularly a biguanide oligomer, and having a pH of less than 5. The biguanide oligomer may be a poly(hexamethylene biguanide) having up to 15 repeat units. The medium has improved storage stability compared to commercially available systems and is at least as effective as a biocide.

6 Claims, No Drawings

AQUEOUS COMPOSITION

This is a continuation of Application Ser. No. 07/784,226, filed Oct. 28, 1991 now abandoned.

The present invention relates to aqueous compositions and particularly to aqueous compositions containing a biguanide, especially a biguanide oligomer.

Biguanides, particularly biguanide oligomers such as hexamethylene biguanide oligomers having up to 15 repeat units, are commercially available materials which can be used as industrial biocides or disinfectants. These materials are typically available in an aqueous medium at a pH of 5 or greater, typically about pH 5.5, and at a concentration of the active ingredient of about 20% by weight relative to the weight of the total composition. It has been found that after a period of time, haze formation can occur and this is generally undesirable and may be unacceptable in some applications.

Hence, it is desirable to provide an aqueous composition containing a biguanide, particularly a biguanide oligomer, which has an improved resistance to the formation of haze.

According to the present invention there is provided an aqueous composition which contains a biguanide and which has a pH of less than 5.

We have found that the pH of aqueous compositions containing biguanides, particularly such compositions containing biguanide oligomers, is dependent on the technique used to measure the pH. Hitherto we have measured, and reported, the pH of aqueous compositions containing biguanides by the use of a pH meter using a glass electrode. However, we have found that the pH so determined can show an upward drift with time and, furthermore, does not correspond to the pH of the same composition as determined using an indicator such as universal indicator. The reason for this difference in the measured pH is believed to be that the aqueous medium is not a true solution but rather one in which the biguanide is present as a second, finely dispersed, phase in the aqueous medium. It is believed that the heterogeneity of such a two phase system is the cause of misleading results obtained when using a glass electrode. Accordingly, unless indicated to the contrary, the term "pH" as used hereafter is the pH obtained using an indicator appropriate for the pH being determined.

The pH of the aqueous composition may be less than 1, for example 0.1 but is typically not less than 2, and generally is at least 3 and especially is at least 4 and less than 5. A pH in the range at least 4 and less than 5 is conveniently measured using bromo-cresol green as the indicator but it will be appreciated that any indicator may be used provided it is appropriate for measurement in the pH range being determined.

A pH of less than 5, as measured using an appropriate indicator, typically has a numerical value which is about one more than the pH of the same composition as measured using a glass electrode. The aqueous composition of the present invention typically has a pH of not more than 4.8 and especially not more than 4.5. We have found that a pH in the range 4 to 4.5 corresponds to a pH of about 3 to 3.5 when determined using a glass electrode.

We have found that the aqueous compositions of the present invention can be stored for a longer period of time than commercially available products with little haze formation. Furthermore, the aqueous compositions when subjected to a microbiological evaluation of activity show essentially the same activity as the commercially available products and in some tests have shown a somewhat greater activity.

The biguanide which is present in the aqueous composition of the present invention contains at least one biguanide unit of the formula (I):

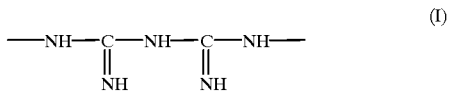

Typically the biguanide contains at least two units of the formula (I) which are linked by a bridging group which contains at least one methylene group. The bridging group may include a polymethylene chain which may optionally be interrupted by hetero atoms such as oxygen, sulphur or nitrogen. The bridging group may include one or more cyclic nuclei which may be saturated or unsaturated. It is generally preferred that the bridging group is such that there are at least three, and especially at least four, carbon atoms directly interposed between two adjacent units of the formula (I). In general it is preferred that there are not more than ten carbon atoms, especially not more than eight carbon atoms, interposed between two adjacent units of the formula (I).

The biguanide units may be terminated by any suitable group which may be a hydrocarbyl or substituted hydrocarbyl group or which may be an amine group or an amine hydrochloride group or by a group

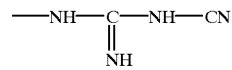

If the terminating group is a hydrocarbyl group this may be an alkyl, cycloalkyl or aryl group or may be a combination thereof as in an aralkyl group. If the terminating group is a substituted hydrocarbyl group, the substituent can be any substituent which does not have an undesirable adverse effect on the microbial activity of the biguanide compound and typically is a hydrocarbonoxy group, a hydrocarboncarbonyl (that is an acyl) group, an ester (that is an acyloxy) group, a halogen atom or a nitrile group and there may be more than one substituent, for example more than one halogen atom.

A suitable biguanide is a material which contains two units of the formula (I) and in which the the units are linked by a polymethylene group, particularly a hexamethylene group. The terminating groups may be 4-chlorophenyl groups, for example as in the compound of formula (II):

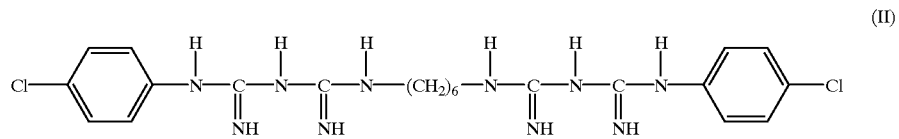

The compound of formula (II) is available as a chlorhexidine salt.

The biguanide may alternatively be a polymeric biguanide, for example a linear polymeric biguanide which has a recurring polymer unit represented by the formula

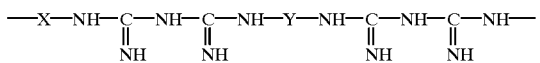

wherein X and Y may be the same or different and represent bridging groups in which together the total number of carbon atoms directly interposed between the pairs of nitrogen atoms linked by X and Y is at least 9 and not more than 17.

The bridging groups X and Y may consist of polymethylene chains, optionally interrupted by hetero atoms, for example, oxygen, sulphur or nitrogen. X and Y may also incorporate cyclic nuclei which may be saturated or unsaturated, in which case the number of carbon atoms directly interposed between the pairs of nitrogen atoms linked by X and Y is taken as including that segment of the cyclic group, or groups, which is the shortest. Thus, the number of carbon atoms directly interposed between the nitrogen atoms in the group

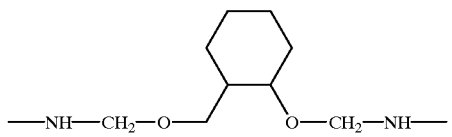

is 4 and not 8.

The preferred polymeric biguanide for use in the present invention is poly(hexamethylene biguanide), in which X and Y both represent the —$(CH_2)_6$— group.

Polymeric biguanides may be prepared by the reaction of a bisdicyanidiamide having the formula

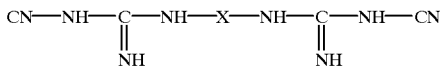

with a diamine $H_2N$—Y—$NH_2$, wherein X and Y have the meanings defined previously herein;

or by reaction between a diamine salt of dicyanimide having the formula

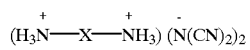

with a diamine $H_2N$—Y—$NH_2$ wherein X and Y have the meanings defined previously herein. These methods of preparation are described in UK Patent Specifications Nos. 702,268 and 1152243 respectively, and any of the polymeric biguanides described therein may be used as the biguanide component of the aqueous composition of the present invention.

The biguanide polymer chains are terminated either by an amino hydrochloride group or by an

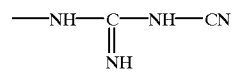

group, and the terminating groups may be the same or different on each polymer chain.

Typically, the polymeric biguanides are obtained as mixtures of polymers in which the polymer chains are of different lengths, the number of individual biguanide units, i.e.

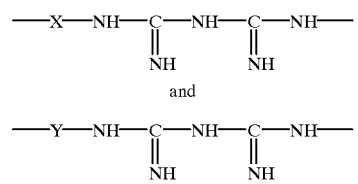

together being from 3 to about 80.

In the case of the preferred poly(hexamethylene biguanide) having the formula (III)

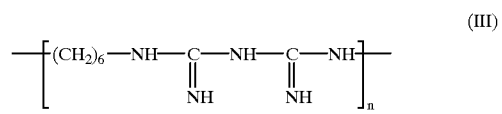

(III)

the value of n is in the range from 4 to 15, the average molecular weight of the polymer mixture being from about 1100 to about 3300.

The biguanides are used as salts with suitable inorganic or organic acids, for example as the hydrochloride salts or the acetate or gluconate.

The preferred aqueous compositions in accordance with the present invention contain a poly(hexamethylene biguanide) of formula III as the hydrochloride salt and have a pH of at least 4 up to 4.5.

The biguanide may be used to provide microbiological protection in an amount of less than 1% w/w, for example in amounts of less than 1000 ppm, especially less than 250 ppm by weight. However, the aqueous compositions of the present invention are typically used as concentrated solutions which can be diluted to a desired level in use. Thus, the biguanide is typically present in the aqueous composition in an amount of at least 1% w/w. In general, the concentration of the biguanide will be at least 5% w/w. The biguanide may be present at concentrations of 25% w/w or even higher but at such concentrations the problem of haze formation is increased. The biguanide is conveniently used at a concentration of about 20% w/w.

We have found the aqueous compositions of the present invention generally show little, if any, haze on being stored for a period of up to two months at ambient temperature in closed drums whereas a similar aqueous composition having a pH in the range 6.5 to 7.0 (about 5.5 using a glass electrode) shows considerable turbidity after being stored for this period of time.

The pH of the aqueous composition may be adjusted to the desired value using a suitable acid or base, typically by the addition of an acid such as hydrochloric acid.

Biguanides have anti-microbial properties and the aqueous compositions of the present invention may be used in any of the applications for which commercially available biguanide compositions have been used or recommended, for example as preservatives for personal-care products, for the protection of hides and skins, and in disinfectants for use in brewing, food processing and the like.

Thus, as a further aspect of the present invention there is provided a method for inhibiting the growth of micro-organisms on, or in, a medium which comprises treating the medium with an aqueous composition containing a biguanide and as hereinbefore defined. The aqueous composition may contain only the biguanide as the anti-microbial agent.

The aqueous composition can be used in conditions in which micro-organisms grow and cause problems. Systems in which micro-organisms cause problems include liquid, particularly aqueous, systems such as cooling water liquors, paper mill liquors, metal working fluids, geological drilling lubricants, polymer emulsions and surface coating compositions such as paints, varnishes and lacquers and also solid materials such as wood and leather. The aqueous composition of the present invention can be included in such materials to provide an anti-microbial effect. The amount of the aqueous composition is typically sufficient to provide a biguanide concentration in the range from 0.0001 up to 10%, preferably 0.0002 up to 5% and especially 0.0002 to 0.1% by weight of biguanide relative to the weight of the system to which it is added. In many cases, microbial inhibition may be obtained with between 0.0005% and 0.05% by weight of the biguanide.

The biguanides which are present in the aqueous composition of the present invention may be the only antimicrobial compounds or may be used together with further compounds having antimicrobial characteristics. The aqueous composition may contain more than one biguanide compound of general formula I. Alternatively, an aqueous composition of a biguanide compound of pH less than 5 in accordance with the present invention may be used together with one or more known antimicrobial compounds. The use of a mixture of anti-microbial compounds can provide a composition having a broader anti-microbial spectrum and hence one which is more generally effective than the components thereof. The known antimicrobial may be one possessing anti-bacterial, anti-fungal, anti-algal or other antimicrobial characteristic. The mixture of the biguanide with other antimicrobial compounds typically contains from 1 to 99% by weight, and particularly from 40 to 60% by weight, relative to the weight of total antimicrobially active compounds, of the mixture of a biguanide compound.

As examples of known antimicrobial compounds which may be used, together with a biguanide compound there may be mentioned quaternary ammonium compounds such as diethyldodecylbenzyl ammonium chloride; dimethyloctadecyl-(dimethylbenzyl)ammonium chloride; dimethyldidecylammonium chloride; dimethyldidodecylammonium chloride; trimethy-tetradecylammonium chloride; benzyldimethyl(($C_{12}$–$C_{18}$ alkyl)ammonium chloride; dichlorobenzyldimethyldodecylammonium chloride; hexadecylpyridinium chloride; hexadecylpyridinium bromide; hexadecyltrimethylammonium bromide; dodecylpyridinium chloride; dodecylpyridinium bisulphate; benzyldodecyl-bis (beta-hydroxyethyl)ammonium chloride; dodecylbenzyltrimethylammonium chloride; benzyldimethyl($C_{12}$–$C_{18}$ alkyl) ammonium chloride; dodecyldimethylethyl ammonium ethylsulphate; dodecyldimethyl-(1-naphthylmethyl)ammonium chloride; hexadecyldimethylbenzyl ammonium chloride; dodecyldimethylbenzyl ammonium chloride and 1-(3-chloroallyl)-3,5,7-triaza-1-azonia-adamantane chloride; urea derivatives such as 1,3-bis(hydroxymethyl)-5,5-dimethylhydantoin; bis(hydroxymethyl)urea; tetrakis (hydroxy-methyl)acetylene diurea; 1-(hydroxymethyl)-5,5-dimethylhydantoin and imidazolidinyl urea; amino compounds such as 1,3-bis(2-ethyl-hexyl)-5-methyl-5-aminohexahydropyrimidine; hexamethylene tetra amine; 1,3-bis(4-aminophenoxy)propane; and 2-[(hydroxymethyl)-amino]ethanol; imidazole derivatives such as 1[2-(2,4-dichloro-phenyl)-2-(2-propenyloxy)ethyl]-1H-imidazole; 2-(methoxycarbonyl-amino)-benzimidazole; nitrile compounds such as 2-bromo-2-bromomethylglutaronitrile, 2-chloro-2-chloromethylglutaronitrile, 2,4,5,6-tetrachloroisophthalodinitrile; thiocyanate derivatives such as methylene bis thiocyanate; tin compounds or complexes such as tributyltin-oxide, chloride, naphthoate, benzoate or 2-hydroxybenzoate; isothiazolin-3-ones such as 4,5-trimethylene-4-isothiazolin-3-one, 2-methyl-4,5-trimethylene-4-isothiazolin-3-one, 2-methylisothiazolin-3-one, 5-chloro-2-methyl-isothiazolin-3-one, benzisothiazolin-3-one and 2-methylbenzisothiazolin-3-one; thiazole derivatives such as 2-(thiocyanomethylthio)-benzthiazole; and mercaptobenzthiazole; nitro compounds such as tris(hydroxymethyl)nitromethane; 5-bromo-5-nitro-1,3-dioxane and 2-bromo-2-nitropropane-1,3-diol; iodine compounds such as iodo propynyl butyl carbamate and tri-iodo allyl alcohol; aldehydes and derivatives such as gluteraldehyde (pentanedial), p-chlorophenyl-3-iodopropargyl formaldehyde, and glyoxal; amides such as chloracetamide; N,N-bis(hydroxymethyl)chloracetamide; N-hydroxymethyl-chloracetamide and dithio-2,2-bis (benzmethyl amide); thiones such as 3,5-dimethyltetrahydro-1,3,5-2H-thiodiazine-2-thione; triazine derivatives such as hexahydrotriazine and 1,3,5-tri-(hydroxyethyl)-1,3,5-hexahydrotriazine; oxazolidine and derivatives thereof such as bis-oxazolidine; furan and derivatives thereof such as 2,5-dihydro-2,5-dialkoxy-2,5-dialkylfuran; carboxylic acids and the salts and esters thereof such as sorbic acid and the salts thereof and 4-hydroxybenzoic acid and the salts and esters thereof; phenol and derivatives thereof such as 5-chloro-2-(2,4-dichloro-phenoxy)phenol; thio-bis(4-chlorophenol) and 2-phenylphenol; sulphone derivatives such as diiodomethyl-paratolyl sulphone, 2,3,5,6-tetrachloro-4-(methylsulphonyl) pyridine and hexachlorodimethyl sulphone.

Further aspects of the present invention are described in the following illustrative examples.

EXAMPLE 1

A commercially available aqueous composition having a pH of 5.3 as measured by a pH meter with a glass electrode, and containing 20% w/w of poly(hexamethylene biguanide) having an average number of repeating units in the range 4–7 was found to have a pH in the range 6.5 to 7.0 as determined by Lyphan pH indicator paper (universal indicator paper).

To a sample of the above aqueous composition was added sufficient concentrated (37%) aqueous hydrochloric acid to give a pH of 3.5 as measured by a pH meter with a glass electrode. The pH of this acidified material was also determined using bromocresol green indicator and was found to be 4.6 by this method. The pH was determined by the addition of 10 drops of 0.04% bromocresol green indicator solution to 50 cm$^3$ of the acidified material in standard 50 cm$^3$ Nessler tubes which were then introduced into a Nessleriser comparator disc apparatus (BDH Lovibond AF 300 Mark 3).

Samples of the commercially available aqueous composition and of the acidified material were stored in 25 kg drums for nine months under ambient conditions (temperature 15–25° C.). After storage, the samples were visually inspected for turbidity. The commercially available aqueous composition showed slight turbidity whilst the acidified material was assessed as "Perfect Clarity".

Six further pairs of samples were prepared essentially as described and were stored for two months. In all cases, the acidified material was assessed as "Perfect Clarity" whilst five samples of the commercially available aqueous composition were assessed as "Turbid" the remaining sample being intermediate between "Slight Turbidity" and "Turbid".

EXAMPLES 2 and 3

The commercially available aqueous composition used in Example 1 was acidified to give samples of pH 4.6 and pH 4.4 (determined using bromocresol green as described). Samples of all three compositions were stored for one month, conditions of storage being as described in Example 1. By visual inspection after one month's storage, the commercially available aqueous composition showed heavy turbidity whilst both acidified materials show perfect clarity.

Three further sets of samples were prepared essentially as described and stored for one month. In all cases, the commercially available aqueous composition was assessed as showing heavy turbidity. One sample of pH 4.6 was assessed as being turbid but all other acidified materials were assessed as showing perfect clarity.

EXAMPLE 4

100 $cm^3$ samples of an aqueous solution containing a range of concentrations of poly(hexamethylene biguanide) were prepared from either the commercially available aqueous composition as used in Example 1 or from an acidified material of pH 4.6 (using bromocresol green indicator). To each sample was added a bacterial inoculum (Escherichia coli) to give a bacterial concentration in the liquid medium of about $1 \times 10^8$ cells/$cm^3$. The samples were placed in 250 $cm^3$ conical flasks, and contained poly(hexamethylene biguanide) at concentrations of 200, 100, 50, 25, 12.5 or 6.25 ppm.

The solutions containing poly(hexamethylene biguanide), together with a solution containing no additive, were incubated at ambient temperature (15°–25° C.). After incubation periods of 10 minutes and one hour, the surviving bacteria were determined by the decimal dilution method using nutrient agar.

The results obtained are set out in the following Table.

TABLE

| Sample | PHMB | Survivors (cells/$cm^3$) | |
|---|---|---|---|
| (a) | Conc. (ppm) (b) | 10 min | one hour |
| 1 | 200 | <10 | <10 |
| 1 | 100 | <10 | <10 |
| 1 | 50 | <10 | <10 |
| 1 | 25 | <10 | <10 |
| 1 | 12.5 | $1.0 \times 10^3$ | <10 |
| 1 | 6.25 | $1.2 \times 10^4$ | <10 |
| A | 200 | <10 | <10 |
| A | 100 | $5 \times 10^1$ | <10 |
| A | 50 | $1.2 \times 10^2$ | <10 |
| A | 25 | $8.6 \times 10^3$ | <10 |
| A | 12.5 | $1.1 \times 10^4$ | <10 |
| A | 6.25 | $3.5 \times 10^5$ | <10 |
| — | NIL | $3.0 \times 10^8$ | $4.5 \times 10^8$ |

Notes to Table
(a)
1 is a acidified poly(hexamethylene biguanide) aqueous solution of pH 4.6
A is a commercially available poly(hexamethylene biguanide) aqueous solution of pH 6.5–7.0.
(b) The concentration is that of the active ingredient, PHMB is poly (hexamethylene biguanide).

EXAMPLES 5 to 7

To different samples of the commercially available aqueous composition described in Example 1 were added sufficient quantities of concentrated (37%) aqueous hydrochloric acid to give materials having a pH of 2.8, 1.8 and 1.0 as determined by bromocresol green, malachite green and malachite green respectively.

50 $cm^3$ samples of each of these acidified materials were placed in jacketed vessels and the contents of each vessel were stirred. The contents of the vessels were subjected to a "freeze-thaw" test by cooling to −8° C. and heating to 15° C. using ethylene glycol as the heat transfer liquid. Heating and cooling were carried out at a rate of 0.6° C. per minute. The temperature of −8° C. was maintained for one minute and the temperature of 15° C. was maintained for 15 minutes. The "freeze-thaw" cycle was effected a total of 15 times.

At the end of 15 cycles, the samples were removed and examined. All the samples were assessed as "Perfect Clarity".

I claim:
1. A method for improving the resistance to haze formation and improved storage stability of an aqueous anti-microbial composition consisting of water and from 5 to 25% by weight of linear polymeric biguanide oligomers having a recurring polymer unit represented by the formula

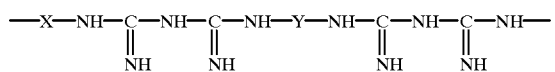

wherein X and Y may be the same or different and represent bridging groups in which together the total number of carbon atoms directly interposed between the pairs of nitrogen atoms linked by X and Y is at least 9 and not more than 17, said method comprising adjusting the pH of said aqueous anti-microbial composition to at least 0.1 and less than 5 as determined using an indicator thereby improving the resistance to haze formation and storage stability of said aqueous anti-microbial composition when compared with a corresponding composition at higher pH.

2. An aqueous anti-microbial composition having improved resistance to haze formation and improved storage stability characteristics, said composition consisting of water and from 5 to 25% by weight of linear polymeric biguanide oligomers having a recurring polymer unit represented by the formula

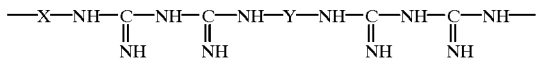

wherein X and Y may be the same or different and represent bridging groups in which together the total number of carbon atoms directly interposed between the pairs of nitrogen atoms linked by X and Y is at least 9 and not more than 17; and which has a pH of at least 0.1 and less than 5 determined using an indicator, and water.

3. The composition of claim 2 which has a pH of at least 4 and less than 5.

4. The composition of claim 2 in which the biguanide is poly(hexamethylene biguanide) having the formula

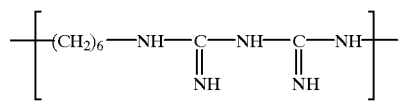

wherein the value of n is from 4 to 15.

5. The composition of claim 4 wherein the poly (hexamethylene biguanide) is in the form of its hydrochloride salt.

6. The composition of claim 2 wherein the indicator is bromo-cresol green.

* * * * *